(12) United States Patent
Kunis

(10) Patent No.: US 7,771,447 B2
(45) Date of Patent: Aug. 10, 2010

(54) BALLOON REFOLDING DEVICE

(75) Inventor: Christopher G. Kunis, Escondido, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 691 days.

(21) Appl. No.: 10/742,162

(22) Filed: Dec. 19, 2003

(65) Prior Publication Data

US 2005/0137618 A1 Jun. 23, 2005

(51) Int. Cl.
*A61M 29/00* (2006.01)
(52) U.S. Cl. ............... 606/194; 606/170; 604/103.14
(58) Field of Classification Search .......... 604/509, 604/96.01, 99.01, 103.06–103.14; 606/159, 606/170, 192, 194
See application file for complete search history.

(56) References Cited

U.S. PATENT DOCUMENTS

| | | | |
|---|---|---|---|
| 4,141,364 A | 2/1979 | Schultze | |
| 4,273,128 A | 6/1981 | Lary | |
| 4,444,186 A | 4/1984 | Wolvek et al. | |
| 4,710,181 A | 12/1987 | Fuqua | |
| 4,723,549 A | 2/1988 | Wholey et al. | |
| 4,784,636 A | 11/1988 | Rydell | |
| 4,881,547 A | 11/1989 | Danforth | |
| 4,921,483 A | 5/1990 | Wijay et al. | |
| 4,941,877 A | 7/1990 | Montano, Jr. | |
| 5,015,230 A | 5/1991 | Martin et al. | |
| 5,015,231 A | 5/1991 | Keith et al. | |
| 5,100,425 A | 3/1992 | Fischell et al. | |
| 5,147,302 A | 9/1992 | Euteneuer | |
| 5,196,024 A * | 3/1993 | Barath ................ | 606/159 |
| 5,209,799 A | 5/1993 | Vigil | |
| 5,221,261 A | 6/1993 | Termin et al. | |
| 5,226,887 A | 7/1993 | Farr et al. | |
| 5,254,091 A | 10/1993 | Aliahmad et al. | |
| 5,318,587 A | 6/1994 | Davey | |
| 5,336,234 A | 8/1994 | Vigil et al. | |
| 5,342,301 A | 8/1994 | Saab | |
| 5,350,361 A | 9/1994 | Tsukashima et al. | |
| 5,456,666 A | 10/1995 | Campbell et al. | |
| 5,458,572 A | 10/1995 | Campbell et al. | |
| 5,478,319 A | 12/1995 | Campbell et al. | |
| 5,490,839 A * | 2/1996 | Wang et al. ............ | 604/103.14 |
| 5,496,276 A * | 3/1996 | Wang et al. ............ | 604/103.06 |
| 5,571,086 A * | 11/1996 | Kaplan et al. ............ | 604/96.01 |
| 5,693,089 A | 12/1997 | Inoue | |

(Continued)

*Primary Examiner*—Nicholas D Lucchesi
*Assistant Examiner*—Theodore J Stigell
(74) *Attorney, Agent, or Firm*—Vidas, Arrett & Steinkraus, P.A.

(57) ABSTRACT

A device for folding a balloon of a balloon catheter onto a catheter tube during a balloon deflation includes a first band positioned on the catheter tube distal to the balloon and a second band positioned on the catheter tube proximal to the balloon. One or more elastic member(s) are attached to and extend between the bands for interaction with the outer surface of the balloon. During a balloon deflation, the elastic members cooperate to fold the balloon into pleats. When used on a cutting balloon, each elastic member is formed with a slot to allow a respective blade of the cutting balloon to extend through the elastic member. The elastic members fold the cutting balloon into a configuration in which each blade becomes nestled within a pair of adjacent balloon pleats to prevent the blade from inadvertently incising tissue during an in-vivo movement of the balloon catheter.

20 Claims, 2 Drawing Sheets

U.S. PATENT DOCUMENTS

| | | |
|---|---|---|
| 5,713,913 A | 2/1998 | Lary et al. |
| 5,718,684 A | 2/1998 | Gupta |
| 5,738,901 A * | 4/1998 | Wang et al. .................. 427/2.3 |
| 5,783,227 A | 7/1998 | Dunham |
| 5,792,158 A | 8/1998 | Lary |
| 5,792,172 A | 8/1998 | Fischell et al. |
| 5,797,935 A * | 8/1998 | Barath ........................ 606/159 |
| 5,853,389 A | 12/1998 | Hijlkema |
| 5,863,284 A * | 1/1999 | Klein ............................ 600/3 |
| 6,013,055 A | 1/2000 | Bampos et al. |
| 6,033,380 A | 3/2000 | Butaric et al. |
| 6,071,285 A | 6/2000 | Lashinski et al. |
| 6,110,192 A | 8/2000 | Ravenscroft et al. |
| 6,126,652 A | 10/2000 | McLeod et al. |
| 6,258,108 B1 | 7/2001 | Lary |
| 6,283,743 B1 | 9/2001 | Traxler et al. |
| 6,425,882 B1 | 7/2002 | Vigil |
| 6,623,451 B2 | 9/2003 | Vigil |
| 6,632,231 B2 * | 10/2003 | Radisch, Jr. ................. 606/159 |
| 7,279,002 B2 * | 10/2007 | Shaw et al. ................ 623/1.11 |
| 2002/0183779 A1 * | 12/2002 | Vigil ........................... 606/192 |
| 2003/0153870 A1 | 8/2003 | Meyer et al. |
| 2005/0021071 A1 * | 1/2005 | Konstantino et al. ......... 606/194 |

* cited by examiner

BALLOON REFOLDING DEVICE

FIELD OF THE INVENTION

The present invention pertains generally to medical catheters. More particularly, the present invention pertains to catheters having inflatable balloons. The present invention is particularly, but not exclusively, useful for folding a balloon onto a catheter tube during a balloon deflation.

BACKGROUND OF THE INVENTION

Arterial blockages caused by the build up of plaque in the arteries of a patient can have grave consequences. Specifically, the build up of plaque in arteries can reduce and eventually block blood flow through the affected vessel. When blood flow is reduced in a coronary artery, the heart muscle becomes deprived of oxygen, and the patient is prone to suffer angina. In severe cases of coronary artery blockage, the patient can suffer a heart attack.

Many modern surgical techniques have been developed to alleviate the stenoses that are formed when plaque builds up in a patient's arteries. For example, a large number of balloon angioplasty devices exist for relieving arterial stenoses by compression of the stenosis. In several respects, balloon angioplasty devices afford numerous advantages over alternative methods. Foremost among these advantages is that open heart bypass surgery can often be avoided by using angioplasty surgical techniques to relieve stenoses in the arteries that supply blood to the heart. For obvious reasons, it is preferable to avoid open heart surgery when possible because such surgery, as is well known, is invasive and typically requires a significant post-operative recovery time. Accordingly, it is preferable to use relatively simpler angioplasty surgical procedures when such procedures are feasible. Importantly, angioplasty procedures are efficacious in the peripheral arteries as well as in the arteries that supply blood to the heart.

In angioplasty surgery, the balloon of a balloon catheter is initially attached to a catheter tube in a deflated configuration, with the catheter tube connecting a fluid source in fluid communication with the balloon. The balloon is then positioned at the desired location in the affected artery by advancing the catheter through the artery until the balloon is positioned across a stenosis that is to be treated. Once the balloon has been properly positioned, fluid is infused into the balloon. As the balloon expands, it dilates the lumen of the artery and compresses the plaque which may then break up or flatten out against the arterial wall. The balloon is then deflated and, once in its deflated configuration, it is either withdrawn from the artery or placed across another stenosis, to restore normal blood flow through the artery.

A particular problem associated with an angioplasty procedure exists during the deflation stage of the balloon, prior to its removal from the artery. Specifically, it is desirable that the balloon be deflated as tightly as practicable to facilitate its removal from the arterial passageways. In any case, the key to removing the balloon catheter with ease is having the balloon collapse evenly and compactly during balloon deflation. Once deflated, the balloon catheter must often travel through the tortuous vasculature of the patient and it is, therefore, important for the balloon to deflate uniformly into a predictable configuration. If the balloon fails to deflate in a uniform manner, an irregular bulge in the balloon may cause difficulties in withdrawing the balloon catheter from the artery.

In addition to the conventional, percutaneous, transluminal coronary angioplasty (PTCA) and percutaneous, transluminal angioplasty (PTA) procedure described above, cutting balloons are currently viewed by many as the next generation treatment option for the revascularization of both coronary and peripheral vessels. The cutting balloon mechanism is unique in that the balloon pressure is distributed over one or more blades (i.e. microtomes). The blade(s) function as stress concentrators and cut initiators in PTCA and PTA procedures. Consequently, PTCA and PTA procedures have been proven to minimize vessel recoil, lessen vessel injury and lower the rate of restenosis, as compared to conventional PTCA and PTA procedures. However, the cutting blades used in cutting balloons are extremely sharp (e.g. three to five times sharper than a conventional scalpel), and in the absence of special precautions, have the potential to inadvertently incise non-target tissue during in vivo movement of the cutting balloon to and from a stenosis.

In light of the above, it is an object of the present invention to provide a device that is useful for folding a balloon predictably and compactly onto a catheter tube during balloon deflation to facilitate in vivo movement of the balloon catheter. Another object of the present invention is to provide a device for maintaining the balloon tightly wrapped on a balloon catheter when the balloon is in a deflated configuration. It is yet another object of the present invention to provide a device that is useful for folding a cutting balloon during balloon deflation into a configuration in which the blades become nestled within a pair of adjacent balloon pleats to prevent the blades from inadvertently incising tissue during an in vivo movement of the balloon catheter. Yet another object of the present invention is to provide a device which is relatively simple to manufacture, easy to use, and comparatively cost effective.

SUMMARY OF THE INVENTION

The present invention is directed to a device for folding a balloon of a balloon catheter onto a catheter tube during a balloon deflation. The device includes a first band that is positioned on the catheter tube distal to the balloon and a second band that is positioned on the catheter tube proximal to the balloon. The device further includes one or more elastic member(s) that are positioned for interaction with the outer surface of the balloon. Each elastic member extends between a distal end that is attached to the first band and a proximal end that is attached to the second band.

In a typical embodiment, the device includes three or four elastic members that are uniformly distributed around the circumference of the balloon. In addition, each elastic member assumes a substantially straight shape and is axially aligned (i.e. aligned with an axis defined by the catheter tube) when the balloon is in a deflated condition. On the other hand, during inflation of the balloon, each elastic member expands on the balloon in substantial conformation with the shape of the balloon's outer surface. When the balloon is subsequently deflated, each elastic member recovers its original shape (e.g. becomes straight), and in the process folds the balloon onto the catheter tube. Specifically, the balloon is folded into a plurality of axially aligned pleats with each pleat being formed between a pair of adjacent elastic members.

In one particular embodiment, the device may be configured for use on a cutting balloon having a plurality of longitudinally aligned blades that extend radially from the surface of an inflatable balloon. In this embodiment, each elastic member is formed with a slot to allow a respective blade to extend through the elastic member. With this cooperation of structure, the elastic members fold the cutting balloon into a configuration in which the blades become nestled within a pair of adjacent balloon pleats. This nestled configuration prevents the blades from inadvertently incising tissue during a movement of the balloon catheter through the vasculature of a patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
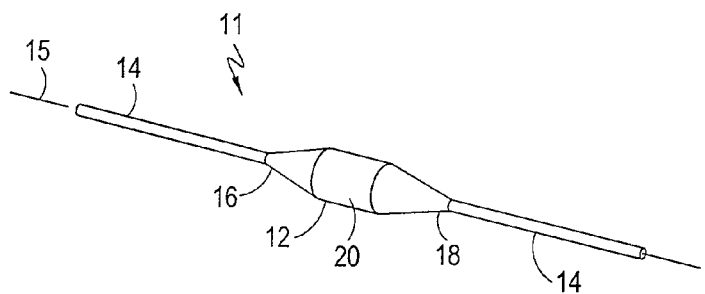
FIG. 1 is a perspective view of a balloon catheter with the balloon shown in the inflated condition.

Referring to FIG. 1, the distal portion of a typical balloon catheter is shown and is generally designated 11. As shown in FIG. 1, the catheter 11 includes an inflatable balloon 12 that is mounted on an elongated catheter tube 14, which defines a longitudinal axis 15. It can be further seen that the exemplary inflatable balloon 12 extends from a distal end 16 to a proximal end 18 and includes a substantially cylindrical working section 20. Those skilled in the pertinent art will appreciate that the catheter tube 14 can be used to establish fluid communication between the inflatable balloon 12 and a fluid pump/fluid source (not shown), which in turn, can be selectively activated to inflate and deflate the balloon 12 from an extracorporeal location. Functionally, the catheter 11 can be used to position the balloon 12 across a stenosis whereupon the balloon 12 can be inflated to revascularize a diseased vessel such as a clogged artery.

Figure 2:
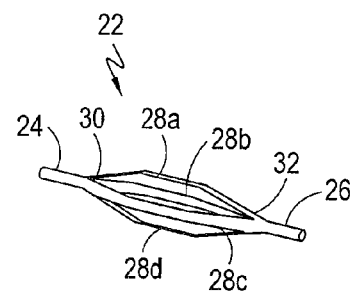
FIG. 2 is a perspective view of a folding device shown in the expanded condition.

FIG. 2 shows a folding device which is generally designated 22. Functionally, the folding device 22 is provided to fold an inflatable balloon 12 (FIG. 1) of a balloon catheter 11 onto a catheter tube 14 during a balloon deflation. As shown in FIG. 2, the folding device 22 includes a first cylindrical band 24, second cylindrical band 26 and a plurality of elastic members 28. For the exemplary embodiment shown, the plurality of elastic members 28 is four elastic members 28a-d. It can be further seen that each elastic member 28 extends between a distal end 30 that is attached to the first band 24 and a proximal end 32 that is attached to the second band 26.

The folding device 22 can be prepared from a starting tube (not shown) that is made of a low durometer, elastic material such as a Silastic® material comprising a silicone elastomer. The tube 14 can then be cut, for example using a laser beam to create the elastic members 28. In some embodiments, a plurality of slits can be cut in the tube. A slit can extend between the cylindrical bands 24, 26, and material between adjacent slits can comprise the elastic members 28. In some methods, the tube 14 can be expanded prior to cutting. In one embodiment, a starting tube 14 having an inner diameter, d, that is larger than the outer diameter, D, of the catheter tube 14 is used. The bands 24, 26 (which have an inner diameter, d, in the relaxed state) are then expanded to fit on the catheter tube 14. The residual tension in the bands 24, 26 is then used to hold the bands 24, 26 in place.

Figure 3:
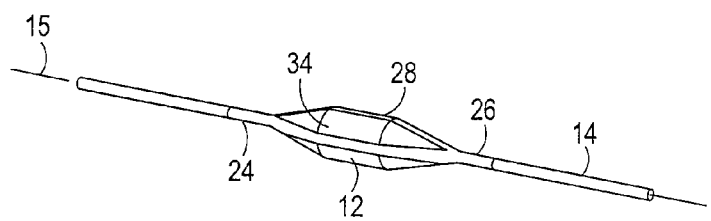
FIG. 3 is a perspective view of a folding device shown operationally positioned on a balloon catheter with the balloon shown in the inflated condition.

FIG. 3 shows the folding device 22 positioned on the balloon catheter 11. As shown, the band 24 is positioned on the catheter tube 14 distal to the balloon 12 and the band 26 is positioned on the catheter tube 14 proximal to the balloon 12. The bands 24, 26 can be bonded to the catheter tube 14, or as indicated above, the bands 24, 26 can be held in place using expanded bands 24, 26. FIG. 3 further shows that with the folding device 22 installed on the balloon catheter 11, the elastic members 28 are positioned for interaction with the outer surface 34 of the balloon 12. For the folding device 22 shown in FIG. 3, the four elastic members 28 are uniformly distributed around the circumference of the balloon 12.

Figure 4:
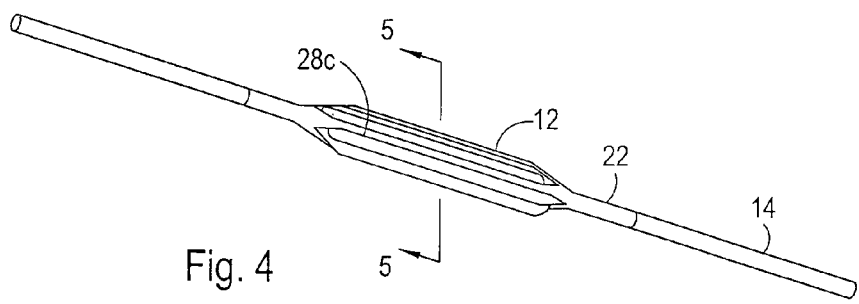
FIG. 4 is a perspective view of a folding device shown operationally positioned on a balloon catheter with the balloon shown in the deflated condition.
Figure 5:
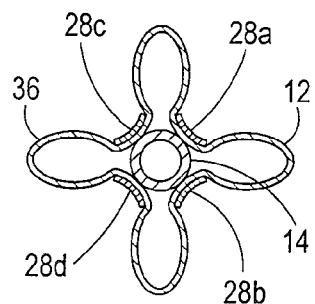
FIG. 5 is a cross sectional view as seen along line 5-5 in FIG. 4.

As best seen in FIG. 4, each elastic member 28 assumes a substantially straight shape and is axially aligned when the balloon 12 is in a deflated condition. On the other hand, during inflation of the balloon 12 (inflated balloon 12 shown in FIG. 3), each elastic member 28 expands (i.e. stretches) on the balloon 12 in substantial conformation with the shape of outer surface 34 of the balloon 12. As best seen in FIG. 5, when the balloon 12 is subsequently deflated, each elastic member 28 recovers its original shape (e.g. becomes straight), and in the process folds the balloon 12 onto the catheter tube 14. Specifically, as shown, the balloon 12 is typically folded into a plurality of axially aligned pleats 36 with each pleat 36 being formed between a pair of adjacent elastic members 28.

Figure 6:
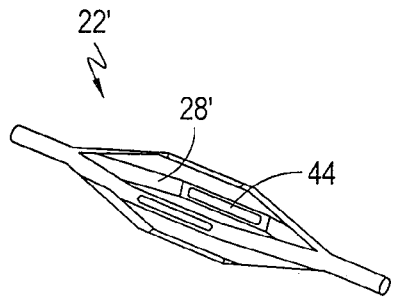
FIG. 6 is a perspective view of an embodiment of a folding device for use on a cutting balloon, shown with the folding device in the expanded condition.
Figure 7:
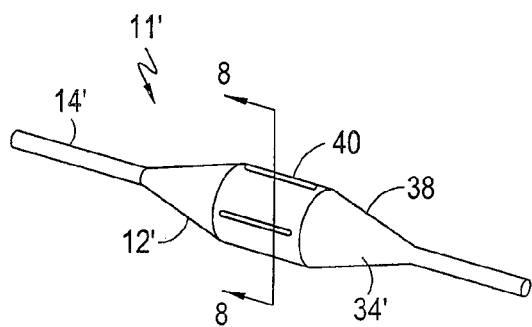
FIG. 7 is a perspective view of a balloon catheter having a cutting balloon, shown with the cutting balloon in the inflated condition.
Figure 8:
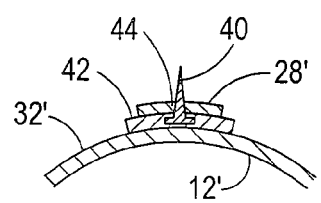
FIG. 8 is a cross sectional view as seen along line 8-8 in FIG. 7 after the folding device shown in FIG. 6 has been operationally positioned on the cutting balloon shown in FIG. 7.

FIG. 6 shows an alternate embodiment of a folding device 22' in which the folding device 22' is configured for use on a balloon catheter 11' (FIG. 7) having a cutting balloon 38 and inflation tube 14'. As further shown in FIGS. 7 and 8, the exemplary cutting balloon 38 has a plurality of longitudinally aligned blades 40 that extend radially from the surface 34' of an inflatable balloon 12'. As best seen in FIG. 8, each blade 40 is typically embedded in a compliant blade pad 42, which in turn is bonded to the surface 32' of the inflatable balloon 12'.

Figure 9:
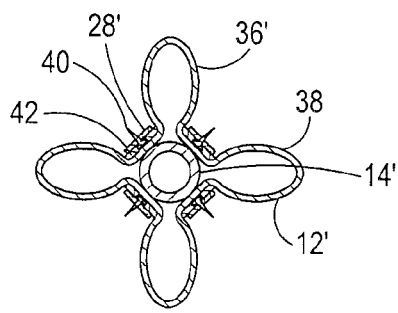
FIG. 9 is a cross sectional view as in FIG. 8 shown with the cutting balloon deflated.

For the folding device 22' shown in FIG. 6, each elastic member 28' is formed with a slot 44, which is typically elongated and axially aligned. Cross-referencing FIGS. 6 and 8, it can be seen that the slot 44 allows a respective blade 40 to extend through the elastic member 28'. As FIG. 9 shows, the elastic members 28' fold the cutting balloon 38 into a configuration in which the blades 40 become nestled within a pair of adjacent balloon pleats 36'. This nestled configuration prevents the blades 40 from inadvertently incising tissue during a movement of the balloon catheter 11' through the vasculature of a patient (patient and patient vasculature not shown).

Figure 10:
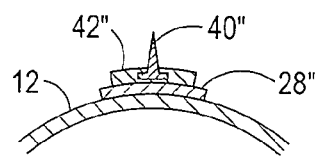
FIG. 10 is a cross sectional view as in FIG. 8 showing another embodiment of a folding device in which blades are mounted on the folding device.

FIG. 10 shows another embodiment in which blades 40" are mounted onto the elastic members 28". For the embodiment shown, the blades 40″ are embedded in blade pads 42″ which in turn are bonded to the elastic members 28″.

While the particular balloon refolding device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A catheter comprising:
    a catheter shaft defining an inflation lumen;
    an inflation balloon in fluid communication with said inflation lumen; and
    an elastic tube comprising a first end band, a second end band and a plurality of slits extending between the first end band and the second end band, the elastic tube positioned over the catheter, at least a portion of the first end band located distal to the inflation balloon, at least a portion of the second end band located proximal to the inflation balloon, said plurality of slits positioned over the inflation balloon;
    wherein a portion of said elastic tube is bonded to a portion of said catheter shaft; and
    wherein, in a deflated state, the balloon is folded by the tube into a plurality of pleats such that each pleat is positioned in a different slit of said plurality of slits.

2. The catheter of claim 1, wherein said balloon is inflated.

3. The catheter of claim 1, wherein said first end band is bonded to a portion of said catheter shaft located distal to the inflation balloon and said second end band is bonded to a portion of said catheter shaft located proximal to the inflation balloon.

4. A balloon catheter comprising:
    a balloon, the balloon defining a balloon length;
    a catheter shaft defining an inflation lumen in fluid communication with said balloon, the catheter shaft comprising a proximal shaft portion located proximal to the balloon and a distal shaft portion located distal to the balloon; and
    an elastic tube, the elastic tube defining a tube length that is greater than said balloon length, the elastic tube comprising a plurality of slits formed therein, a length of each slit being less than said tube length, wherein a proximal portion of said elastic tube is positioned around said proximal shaft portion, a central portion of said elastic tube is positioned around said balloon, and a distal portion of said elastic tube is positioned around said distal shaft portion;
    wherein a portion of said elastic tube is bonded to the catheter shaft; and
    wherein, in a deflated state, the balloon is folded by the tube inot a plurality of pleats such that each pleat is positioned in a different slit of said plurality of slits.

5. The balloon catheter of claim 4, wherein said balloon catheter excludes cutting blades.

6. The balloon catheter of claim 4, wherein when said balloon is inflated, said elastic tube proximal portion remains positioned around said proximal shaft portion, and said elastic tube distal portion remains positioned around said distal shaft portion.

7. The balloon catheter of claim 4, wherein said elastic tube distal portion is bonded to said distal shaft portion.

8. The balloon catheter of claim 7, wherein said elastic tube proximal portion is bonded to said proximal shaft portion.

9. The balloon catheter of claim 4, further comprising a cutting blade mounted on said elastic tube.

10. The balloon catheter of claim 4, wherein an unstressed inner diameter of said elastic tube is less than a diameter of said catheter shaft.

11. A balloon catheter comprising:
    a balloon, the balloon defining a balloon length;
    a catheter shaft, the catheter shaft comprising a proximal shaft portion located proximal to the balloon and a distal shaft portion located distal to the balloon; and
    an elastic tube, the elastic tube defining a tube length that is greater than said balloon length, the elastic tube comprising a plurality of slits formed therein, a length of each slit being less than said tube length, wherein a proximal portion of said elastic tube is positioned around said proximal shaft portion, a central portion of said elastic tube is positioned around said balloon, and a distal portion of said elastic tube is positioned around said distal shaft portion;
    wherein said balloon further comprises a plurality of cutting blades, and said elastic tube central portion further comprises a plurality of slots, each slot extending through a full radial wall height of the elastic tube.

12. The balloon catheter of claim 11, wherein each cutting blade passes through a slot.

13. The balloon catheter of claim 11, wherein a length of a slot is less than the length of a slit.

14. A method comprising:
    providing a balloon catheter comprising a balloon and a catheter shaft, the balloon defining a balloon length, the catheter shaft comprising a proximal shaft portion located proximal to the balloon and a distal shaft portion located distal to the balloon;
    providing an elastic tube, the elastic tube defining a tube length that is greater than said balloon length, the elastic tube comprising a proximal portion, a central portion and a distal portion, the central portion comprising a plurality of slits;
    positioning said elastic tube around said balloon catheter such that said elastic tube proximal portion is positioned around said proximal shaft portion, said elastic tube central portion is positioned around said balloon, and said elastic tube distal portion is positioned around said distal shaft portion;
    arranging the balloon such that the balloon is folded into a plurality of pleats, each pleat being positioned in a different slit of said plurality of slits; and
    bonding a portion of said elastic tube to a portion of said catheter shaft.

15. The method of claim 14, wherein providing an elastic tube further comprises providing a unitary elastic tube and forming said plurality of slits therein.

16. The method of claim 15, wherein said slits are formed with a laser.

17. The method of claim 14, wherein said bonding step comprises bonding said elastic tube distal portion to said distal shaft portion.

18. The method of claim 17, wherein said bonding step further comprises bonding said elastic tube proximal portion to said proximal shaft portion.

19. A method comprising:
    providing a balloon catheter comprising a balloon and a catheter shaft, the balloon defining a balloon length, the catheter shaft comprising a proximal shaft portion located proximal to the balloon and a distal shaft portion located distal to the balloon;
    providing an elastic tube, the elastic tube defining a tube length that is greater than said balloon length, the elastic tube comprising a proximal portion, a central portion and a distal portion, the central portion comprising a plurality of slits;

positioning said elastic tube around said balloon catheter such that said elastic tube proximal portion is positioned around said proximal shaft portion, said elastic tube central portion is positioned around said balloon, and said elastic tube distal portion is positioned around said distal shaft portion;

wherein said balloon further comprises a plurality of cutting blades and said elastic tube further comprises a plurality of slots, each slot extending through a full radial wall height of the elastic tube, the method further comprising positioning the elastic tube such that each cutting blade extends through a slot.

20. The method of claim 19, wherein providing an elastic tube further comprises forming said slots therein.

\* \* \* \* \*

UNITED STATES PATENT AND TRADEMARK OFFICE
CERTIFICATE OF CORRECTION

PATENT NO. : 7,771,447 B2  
APPLICATION NO. : 10/742162  
DATED : August 10, 2010  
INVENTOR(S) : Christopher G. Kunis Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this
Fourth Day of June, 2013

Teresa Stanek Rea
*Acting Director of the United States Patent and Trademark Office*